United States Patent
Scheiner et al.

(10) Patent No.: US 7,201,733 B2
(45) Date of Patent: Apr. 10, 2007

(54) DRUG DELIVERY SYSTEM FOR IMPLANTABLE CARDIAC DEVICE

(75) Inventors: Avram Scheiner, Vadnais Heights, MN (US); Mark Herner, Indianapolis, IN (US); Ronald W. Heil, Jr., Roseville, MN (US); Steven D. Girouard, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 385 days.

(21) Appl. No.: 09/999,260

(22) Filed: Nov. 30, 2001

(65) Prior Publication Data

US 2002/0099328 A1 Jul. 25, 2002

Related U.S. Application Data

(63) Continuation of application No. 09/422,433, filed on Oct. 21, 1999, now Pat. No. 6,361,522.

(51) Int. Cl.
*A61M 31/00* (2006.01)

(52) U.S. Cl. ....................................................... 604/67

(58) Field of Classification Search ................ 128/899, 128/897–898, 903, DIG. 12, DIG. 13; 600/509, 600/300, 510; 607/9, 28; 604/50–53, 65–67
See application file for complete search history.

(56) References Cited

U.S. PATENT DOCUMENTS

| | | | | |
|---|---|---|---|---|
| 3,692,027 | A | 9/1972 | Ellinwood, Jr. | 128/260 |
| 4,003,379 | A | 1/1977 | Ellinwood, Jr. | 128/260 |
| 4,146,029 | A | 3/1979 | Ellinwood, Jr. | 128/260 |
| 4,281,664 | A | 8/1981 | Duggan | 128/696 |
| 4,299,220 | A | 11/1981 | Dorman | 128/260 |
| 4,544,371 | A | 10/1985 | Dormandy, Jr. et al. | 604/891 |
| 4,556,063 | A | 12/1985 | Thompson et al. | 128/419 PT |
| 4,561,443 | A * | 12/1985 | Hogrefe et al. | 607/31 |
| 4,686,987 | A | 8/1987 | Salo et al. | 128/419 PG |
| 4,871,351 | A * | 10/1989 | Feingold | 604/66 |
| 4,897,987 | A | 2/1990 | Spalla | 56/16.7 |
| 4,944,299 | A | 7/1990 | Silvian | 128/419 PG |
| 4,987,897 | A | 1/1991 | Funke | 128/419 PG |
| 5,014,698 | A * | 5/1991 | Cohen | 607/4 |
| 5,040,533 | A | 8/1991 | Fearnot | 128/419 PG |
| 5,041,107 | A | 8/1991 | Heil, Jr. | 604/891.1 |
| 5,042,497 | A | 8/1991 | Shapland | 128/696 |
| 5,058,581 | A | 10/1991 | Silvian | 128/419 PG |
| 5,087,243 | A | 2/1992 | Avitall | 604/20 |
| 5,127,404 | A | 7/1992 | Wyborny et al. | 128/419 P |
| 5,190,035 | A | 3/1993 | Salo et al. | 128/419 |

(Continued)

FOREIGN PATENT DOCUMENTS

EP 0054138 10/1981

OTHER PUBLICATIONS

Sweeney, Robert J., et al., "Drug Delivery System for Implantable Medical Device", U.S. Appl. No. 10/743,507, filed Dec. 22, 2003, 17 pgs.

*Primary Examiner*—Manuel Mendez
(74) *Attorney, Agent, or Firm*—Schwegman, Lundberg, Woessner, & Kluth, P.A.

(57) ABSTRACT

A drug delivery system incorporated into a cardiac device for delivering a dose of a drug to a patient upon detection of a particular medical condition. The cardiac device may be, for example, an implantable cardioverter/defibrillator, cardiac pacemaker, or combination device that communicates via a radio frequency link with a drug delivery device. The drug delivery device is preferably an electrically modulated transdermal drug delivery device for delivering the drug transdermally in accordance with a signal received from the cardiac device.

18 Claims, 2 Drawing Sheets

U.S. PATENT DOCUMENTS

| | | |
|---|---|---|
| 5,220,917 A | 6/1993 | Cammilli et al. ........ 128/419 D |
| 5,269,301 A | 12/1993 | Cohen ........................... 607/6 |
| 5,284,136 A | 2/1994 | Hauck et al. .................. 607/24 |
| 5,305,745 A | 4/1994 | Zacouto ...................... 128/637 |
| 5,342,408 A | 8/1994 | deCoriolis et al. ............. 607/32 |
| 5,368,028 A | 11/1994 | Palti ........................... 128/635 |
| 5,416,695 A | 5/1995 | Stutman et al. ........ 364/413.02 |
| 5,456,692 A | 10/1995 | Smith, Jr. et al. ............. 607/31 |
| 5,460,605 A | 10/1995 | Tuttle et al. ................... 604/67 |
| 5,496,360 A | 3/1996 | Hoffmann et al. ........... 607/120 |
| 5,551,953 A * | 9/1996 | Lattin et al. ................... 604/20 |
| 5,556,421 A | 9/1996 | Prutchi et al. ................. 607/36 |
| 5,562,713 A | 10/1996 | Silvian ........................... 607/32 |
| 5,579,876 A | 12/1996 | Adrian et al. .......... 188/322.17 |
| 5,586,556 A | 12/1996 | Spivey et al. ............... 128/697 |
| 5,607,418 A | 3/1997 | Arzbaecher .............. 604/891.1 |
| 5,690,682 A | 11/1997 | Buscemi et al. ................ 607/3 |
| 5,693,075 A | 12/1997 | Plicchi et al. .................. 607/17 |
| 5,720,770 A | 2/1998 | Nappholz et al. .............. 607/30 |
| 5,730,125 A | 3/1998 | Prutchi et al. ............... 128/637 |
| 5,836,935 A | 11/1998 | Ashton et al. ............ 604/891.1 |
| 5,893,881 A | 4/1999 | Elsberry et al. ................ 607/5 |
| 5,899,928 A | 5/1999 | Sholder et al. ................ 607/27 |
| 5,925,066 A | 7/1999 | Kroll et al. ..................... 607/3 |
| 6,016,443 A | 1/2000 | Ekwall et al. |
| 6,112,116 A | 8/2000 | Fischell et al. |
| 6,115,636 A | 9/2000 | Ryan ........................... 607/60 |
| 6,155,267 A * | 12/2000 | Nelson ....................... 128/899 |
| 6,264,606 B1 | 7/2001 | Ekwall et al. |
| 6,361,522 B1 | 3/2002 | Scheiner et al. ............ 604/67 |
| 6,453,195 B1 | 9/2002 | Thompson ..................... 607/3 |
| 6,628,985 B2 | 9/2003 | Sweeney et al. ............ 600/510 |
| 6,689,117 B2 | 2/2004 | Sweeney et al. ............ 604/503 |
| 2004/0059391 A1 | 3/2004 | Sweeney et al. .............. 607/27 |
| 2004/0093034 A1 | 5/2004 | Girouard et al. ................ 607/3 |

* cited by examiner

DRUG DELIVERY SYSTEM FOR IMPLANTABLE CARDIAC DEVICE

CROSS REFERENCE TO RELATED APPLICATIONS

This application is a continuation of U.S. patent application Ser. No. 09/422,433, filed on Oct. 21, 1999 now U.S. Pat. No. 6,361,522, the specification of which incorporated herein by reference.

FIELD OF THE INVENTION

This invention pertains to systems and methods for drug delivery and the therapeutic application of electrical stimulation to the heart for pacing and/or defibrillation. In particular, the invention relates to a system and method for combining these two modes of therapy.

BACKGROUND

Cardiac pacemakers are implantable devices that replace or supplement a heart's compromised ability to pace itself (i.e., bradycardia) due to chronotropic incompetence or a conduction system defect by delivering electrical pacing pulses to the heart. Implantable cardioverter/defibrillators (ICD's) are devices that deliver electrical energy to the heart in order to reverse excessively rapid heart rates (tachycardia) including life threatening cardiac arrhythmias such as ventricular fibrillation. Since some patients have conditions that necessitate pacing and also render them vulnerable to life-threatening arrhythmias, implantable cardiac devices have been developed that combine both functions in a single device.

Most pacemakers today are operated in some sort of synchronous mode where the pacing pulses are delivered in a manner that is dependent upon the intrinsic depolarizations of the heart as sensed by the pacemaker. ICD's must also sense the electrical activity of the heart in order to detect an arrhythmia that will trigger delivery of the shock pulse in an attempt to reverse the condition. Such sensing information could be used to initiate another mode of therapy, and efforts have been made in the past to combine automatic drug delivery with either pacemakers, ICD's, or both to treat cardiac arrhythmias. U.S. Pat. No. 5,269,301, for example, deals with a system for delivering multi-modal therapy at the patient's bedside in order to treat heart conditions in which pacing, defibrillation, and drug delivery are under the control of a central processor. U.S. Pat. No. 5,087,243 discusses a drug delivery device incorporated into an ICD for delivering an antiarrhythmic drug iontophoretically directly to the myocardium via the patch electrodes used for electrical defibrillation upon detection of an arrhythmia. U.S. Pat. No. 5,893,881 describes an ICD with an integrated drug delivery device for delivery of a pain medication just prior to the delivery of a defibrillation shock. That patent also contemplates a separate implantable drug delivery device that communicates with the ICD via low-frequency radio waves transmitted through the body using a method described in U.S. Pat. No. 4,897,987.

Implantable drug delivery systems suffer from a number of disadvantages, however. Although the drug reservoir of such a device can be replenished, it is difficult to change the drug once it is put into the reservoir, making patient management difficult in cases where a patient's condition either changes or otherwise requires a change of medication. In addition, drugs degrade over time. Finally, there is the risk of leakage from the reservoir, the consequences of which can range from an annoyance to a medical emergency.

SUMMARY OF THE INVENTION

The present invention is embodied by a drug delivery system incorporated into an cardiac device which may be, for example, an implantable cardioverter/defibrillator, cardiac pacemaker, or combination device. A dose of a drug is delivered by the system to a patient upon detection of a particular medical condition such as an arrhythmia. The drug delivery device is preferably an electrically modulated transdermal drug delivery device for delivering the drug transdermally in accordance with a signal received from the implantable cardiac device. The implantable cardiac device communicates via a radio frequency link with the external drug delivery device.

In one embodiment, an external drug delivery device is designed for external affixation to a patient. In the case of an electrically modulated transdermal drug delivery device, the device is affixed to the patient's skin surface at a suitable location. The electrically modulated transdermal delivery injector may have one electrode with a drug reservoir in contact with the skin, another electrode also contacting the skin, and a voltage source for imposing a voltage between the electrodes. The device also has a telemetry interface for receiving and transmitting radio frequency signals, circuitry for demodulating radio signals received from the implantable cardiac device or an external programmer to derive a command signal therefrom, and circuitry for controlling the delivery of the drug in accordance with the command signal.

The cardiac device has at least one sensing channel for sensing electrical activity occurring in a patient's heart and generating sensing signals indicative of the activity. Circuitry in the device extracts information from the sensing signals, which information can be used to detect a particular medical condition, and a command signal is generated if the medical condition is present. A telemetry interface for receiving and transmitting radio frequency signals to the drug delivery device is also provided, along with circuitry for modulating the radio frequency signals with information relating to the command signal.

In another aspect of the invention, an implantable cardiac device with an incorporated drug delivery system is used to detect cardiac ischemia from the sensed electrical activity as well as arrhythmias. Upon detection of a cardiac event correlated with ischemia, the device causes delivery of an appropriate agent such as a thrombolytic, anti-platelet agent, coronary vasodilator, anticoagulant, analgesic, or combination of such agents.

DESCRIPTION OF A SPECIFIC EMBODIMENT

In the embodiment to be described, the operations of the implantable cardiac device and the drug delivery device are each controlled by circuitry which includes a microprocessor executing programmed instructions in memory. Certain functions could be controlled by custom logic circuitry either in addition to or instead of a programmed microprocessor. The term "circuitry" as used herein should therefore be taken to mean either custom circuitry (i.e., dedicated hardware) or a microprocessor executing programmed instructions contained in a processor-readable storage medium along with associated circuit elements.

Figure 1:
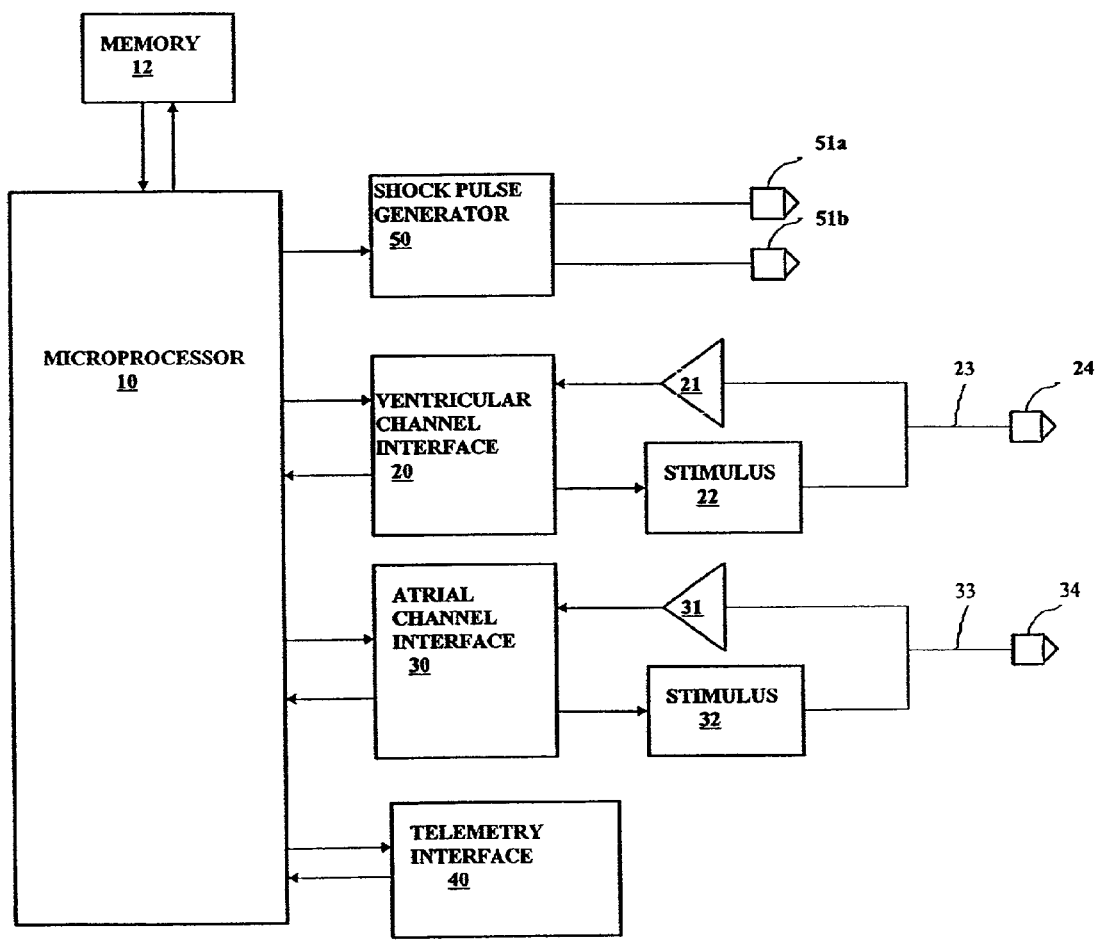
FIG. 1 is a system diagram of an exemplary implantable cardiac device.

FIG. 1 is a system diagram of a microprocessor-based implantable cardioverter/defibrillator with the capability of also delivering pacing therapy. A microprocessor 10 communicates with a memory 12 via a bidirectional data bus. The memory 12 typically comprises a ROM for program storage and a RAM for data storage. The device has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. (The sensing and pacing channels in this embodiment use unipolar leads with one electrode attached to each lead and with the case of the device being utilized as a second electrode for each channel. Other embodiments may use bipolar leads with two electrodes attached to each lead.) The channel interfaces 20 and 30 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. For each channel, the same lead and electrode are used for both sensing and pacing. The sensing channels are used in conjunction with pacing and for measuring heart rate in order to detect tachycardia and fibrillation. A shock pulse generator 50 is also interfaced to the microprocessor for delivering cardioversion or defibrillation pulses to the heart via a pair of electrodes 51a and 51b. (In other embodiments, alternative shock electrode configurations well-known in the art could be used.) A telemetry interface 40 enables the device to communicate with an external programmer via modulated radio frequency waves as well as transmit a command signal to the drug delivery device upon detection of a particular medical condition such as an arrhythmia. (An external programmer in this context refers to a type of device for communicating with an implanted device to in order to issue commands affecting its operation or to retrieve status and/or logged information.)

Figure 2:
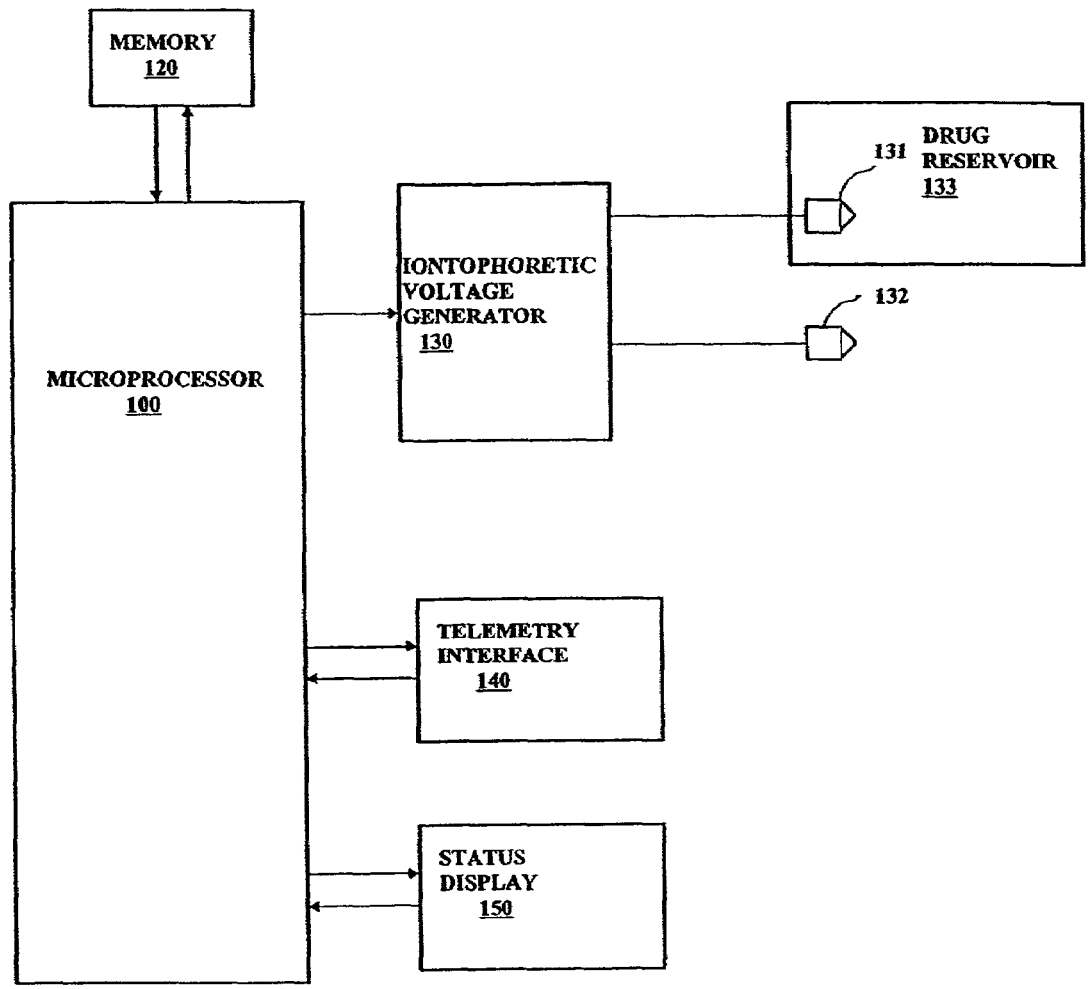
FIG. 2 is system diagram of the drug delivery device.

FIG. 2 is a system diagram of an external drug delivery device for delivering a quantity of a drug in accordance with a command signal received from the implantable cardiac device. The control circuitry of the drug delivery device is similar to the implantable cardiac device including a microprocessor 100, memory 120, and a telemetry interface 140 for receiving and demodulating radio signals received from the cardiac device or from an external programmer. A status display 150 is also interfaced to the microprocessor for displaying information to a user relating to the device's operating status such as battery power remaining, the amount of drug in the reservoir, and a log of previous drug deliveries including the amount of drug delivered. Such information can also be transmitted either to the implanted cardiac device or an external programmer upon receipt of an appropriate query command.

Also interfaced to the microprocessor is a electrically modulated transdermal drug delivery voltage generator 130 for generating a voltage between electrodes 131 and 132. Electrode 131 is electrically connected to a drug reservoir 133 which is adapted for contacting the patient's skin. The term "electrically modulated transdermal drug delivery device" is meant to include any device that uses an electrical field to controllably deliver drugs transdermally such as by e.g., iontophoresis, electroporation, electrorepulsion, or electro-osmosis. Electrode 132 is also adapted for contacting the patient's skin so that when a voltage is impressed across the electrodes, charged drug molecules are caused to migrate from the reservoir 133 through epidermal appendages and pores into the dermal capillary bed where the drug then diffuses into the circulation. The drug may be in the form of an aqueous solution whose pH is adjusted so that most of the drug is in a charged form, with the polarity of the electrodes 131 and 132 adjusted for whether the drug is in anionic or cationic form. The drug solution may then be contained in the reservoir by any medium capable of holding the drug and allowing its free flow when subject to an electrical field such as a gauze patch, or a gel or solution with a porous wrapping. The reservoir 133 is preferably mounted in a frame suitable for affixation to the patient such that the reservoir is in contact with skin.

In another embodiment, both electrodes are connected to drug reservoirs so that drugs can be simultaneously delivered from both electrodes. In such a configuration, a drug that is positively charged in solution is delivered from the anode (i.e., the positively charged electrode) while a second drug that is negatively charged in solution is delivered from the cathode. Multiple drug concoctions of similar polarity can also be placed in the respective anodic or cathodic drug reservoir for simultaneous delivery. In another embodiment, the same drug is placed in both reservoirs, with the pH of the solution containing the drug adjusted in each reservoir so that the drug assumes the appropriate charge for delivery from the electrode connected to that reservoir. That is, the pH of the solution is adjusted in each reservoir to be above or below the pK of the drug.

In operation, the cardiac device detects a particular medical condition such as an arrhythmia by an analysis of the digitized information received from the sensing channels according to algorithms implemented by the programmed microprocessor 10. Upon detection of a particular condition indicating the need for drug delivery, a command signal is generated which consists of a coded message suitable for transmission via the telemetry interface 40. The command signal is then used to modulate a carrier signal which is received by the drug delivery device. Such a command signal can also be generated and transmitted by an external programmer. Upon demodulation of the carrier signal to derive the command signal, the electrically modulated transdermal drug delivery voltage generator 130 is activated by the microprocessor 100 to deliver a quantity of the drug to the patient. The command signal can also contain information relating to the amount of drug that is to be delivered by the drug delivery device and/or the time period over which the delivery is to take place. In a preferred embodiment, after receipt of the command signal, the drug delivery device generates a status signal that is transmitted back to the implanted cardiac device or external programmer to acknowledge the command. A status signal is similarly generated and transmitted after the drug delivery operation to verify that the drug has been delivered in accordance with the command. Analysis of further sensing data by the cardiac device in a accordance with programmed algorithms then allows the effectiveness of the therapy in alleviating the detected medical condition to be assessed and logged.

In another aspect of the invention, drugs other than anti-arrhythmics can be employed in a drug delivery system such as described above to treat myocardial ischemia. Most patients today who are in need of an implantable cardioverter/defibrillator or pacemaker also suffer from coronary atherosclerotic disease which predisposes to acute occlusive events due to thrombus formation within the arterial lumina. Since such events may precipitate lethal arrhythmias, it may be desirable in certain patients in whom such arrhythmias are correlated with ischemic events to deliver an anti-ischemia agent to directly affect the occlusive process such as a thrombolytic, an anticoagulant, an anti-platelet agent, or a vasodilator when an arrhythmic condition is detected. In another embodiment, data from the sensing channels is analyzed to detect a current of injury in the sensed electrical activity of the heart which indicates myocardial ischemia. Upon detection of such an ischemic event by the cardiac device, an anti-ischemia agent is delivered by the drug delivery system.

In another embodiment, the drug or drugs contained in the drug reservoir may be the same agents as currently being taken orally (or otherwise) by the patient. The system would detect an arrhythmia or other treatable event that may be caused by the body concentration of the orally administered drug falling below a therapeutic concentration. Once this event is detected, a signal from the implantable device causes prompt delivery of the same agent from the external reservoir to restore a therapeutic concentration of the drug. Electrical therapy would also be available if needed during this transient recovery period.

In another embodiment, an external drug delivery device as described above is used to initiate treatment of a patient with a drug or drugs where the optimum dosage is not known at the outset. By incorporating a sensor or sensors for measuring or detecting a physiological variable in the drug delivery device, or in a separate device in communication with the drug delivery device, a feedback loop is formed that enables the device to find the drug dosage that produces the desired physiological effect as detected by the sensors. For example, a blood pressure medication may be administered by the drug delivery device, with the drug delivery device in communication with a means for continuously measuring blood pressure such as a tonometric manometer. The drug delivery device would then be programmed to deliver the drug in an amount that attempts to maintain the blood pressure within a specified range. Similarly, an antiarrhythmic drug could be delivered by an external drug delivery device that is in communication with a cardiac sensor for detecting arrhythmias. The drug delivery device would then attempt to administer an amount of the drug that prevents the occurrence of arrhythmias, increasing or decreasing the amount in accordance with whether or not arrhythmias are detected by the cardiac sensor. The drug delivery device would maintain a log of detected events and/or measured physiological variables along with the amount of drug delivered over a specified time period. By downloading the log from the drug delivery device (e.g., either with a direct connection or over a telemetry link), a treating physician is able to obtain a record of the response of the patient over time to the administered drug and formulate an optimum drug dosage schedule for the patient. The drug dosage for the patient may then be continued, either with the external drug delivery device, or with a schedule of drug dosages administered orally or otherwise.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A drug delivery system comprising:
    an implantable cardiac device having incorporated therein a sensor for sensing a physiological variable in a patient, a first telemetry interface for transmitting radio frequency signals, and circuitry for modulating the radio frequency signals with a drug delivery command signal;
    an external drug delivery device for affixation to a skin surface location on the patient, the drug delivery device having incorporated therein a second telemetry interface for receiving radio frequency signals, circuitry for demodulating radio signals to derive a drug delivery command signal therefrom, and circuitry for controlling the drug delivery device in order to deliver a drug upon receipt of a drug delivery command signal;
    wherein the implantable cardiac device is programmed to transmit a drug delivery command signal to the external drug delivery device in response to the sensed physiological variable in a manner that attempts to control the sensed variable in a closed-loop fashion; and,
    wherein the system is programmed to maintain a downloadable log of the sensed physiological variable and of the amount of drug administered by the drug delivery device that can be used to formulate an optimum drug dosage schedule for the patient.

2. The system of claim 1, wherein the implantable cardiac device includes a cardioverter/defibrillator.

3. The system of claim 1, wherein the implantable cardiac device includes a pacemaker.

4. The system of claim 1, wherein the external drug delivery device is an electrically modulated transdermal injector comprising:
    a first drug reservoir containing a first drug;
    a first electrode, connected to the first drug reservoir, for contacting the patient's skin;
    a second electrode for contacting the patient's skin; and
    a controllable power source, connected to the first and second electrodes, to impose a voltage between the first and second electrodes.

5. The system of claim 4, wherein the transdermal injector further comprises a second drug reservoir containing a second drug, the second electrode is connected to the second drug reservoir, and the first and second drugs are simultaneously delivered, respectively from the first and second drug reservoirs.

6. The system of claim 5, wherein the pH of a solution containing the drug in each reservoir is separately adjusted in accordance with the polarity of the electrode to which the reservoir is connected.

7. The system of claim 1, wherein the drug delivered by the drug delivery device is a vasodilator.

8. The system of claim 1, wherein the drug delivered by the drug delivery device is a thrombolytic.

9. The system of claim 1, wherein the drug delivered by the drug delivery device is an anti-platelet agent.

10. The system of claim 1, wherein the drug delivered by the drug delivery device is an anti-arrhythmic.

11. A method for drug delivery comprising;
    sensing a physiological variable in a patient with an implantable cardiac device;
    generating a command signal with the implantable cardiac device in response to the sensed physiological variable in a manner that attempts to control the sensed variable in a closed-loop fashion;

transmitting the command signal with the implantable cardiac device to an external drug delivery device affixed to a skin surface location on the patient via a radio telemetry link;

receiving the command signal with the external drug delivery device;

delivering a drug with the external drug delivery device based on the command signal;

downloading a log of the sensed physiological variable and of the amount of drug administered by the drug delivery device; and, using the downloaded log to formulate an optimum drug dosage schedule for the patient.

12. The method of claim 11, wherein the implantable cardiac device includes a cardioverter/defibrillator.

13. The method of claim 11, wherein the implantable cardiac device includes a pacemaker.

14. The method of claim 11, further comprising delivering the drug by electrically modulated transdermal injection.

15. The method of claim 11, wherein the drug delivered by the drug delivery device is a vasodilator.

16. The method of claim 11, wherein the drug delivered by the drug delivery device is an anti-arrhythmic.

17. The method of claim 11, wherein the drug delivered by the drug delivery device is a thrombolytic.

18. The method of claim 11, wherein the drug delivered by the drug delivery device is an anti-platelet agent.

* * * * *